United States Patent [19]

Verkade et al.

[11] Patent Number: 5,260,436
[45] Date of Patent: Nov. 9, 1993

[54] METHOD FOR SYNTHESIS OF TRIARYLISOCYANURATES FROM ARYL ISOCYANATES USING TRIAZAPROPHOSPHATRANE CATALYSTS

[75] Inventors: John G. Verkade; Jiansheng Tang, both of Ames, Iowa

[73] Assignee: Iowa State University Research Foundation, Inc., Ames, Iowa

[21] Appl. No.: 5,231

[22] Filed: Jan. 15, 1993

Related U.S. Application Data

[63] Continuation-in-part of Ser. No. 948,168, Sept. 21, 1992, abandoned.

[51] Int. Cl.$^5$ .................................. C07D 251/34
[52] U.S. Cl. ........................................ 544/193
[58] Field of Search ........................... 544/193

[56] References Cited

U.S. PATENT DOCUMENTS 5,051,533  9/1991  Verkade .................. 564/13

FOREIGN PATENT DOCUMENTS 1226878  9/1989  Japan.
3109382  5/1991  Japan.

OTHER PUBLICATIONS

K. Ashide, "Silcate Catalysts for the Formation of Isocyanurates", *Chem. Abs.*, 107, Abs. No. 107:134825j (1987).

Z. Bukac et al., *Chem. Prum.*, 35(7), 361–363 (1985) with English language abstract (Z. Bukac et al., *Chem. Abs.*, 103, Abs. No. 103:123978c (1985)).

Z. Bukac, et al., "Refining of the Cyclic Trimer of Phenyl Isocyanate", Czechoslovkian Patent No. 227,247, *Chem. Abs.*, 105, 10–11, Abs. No. 105:173224r (1986).

D. Gudat et al., *Phosphorus, Sulfur and Silica*, 41, 21–29 (1989).

D. K. Hoffman, *J. Cell. Plast.*, 129–137 (Mar./Apr.: 1984).

J. Horsky et al., *Chem. Prum.*, 32, 599–602 (1982) with English language translation (V. Kubanek et al., *Chem. Prum.*, 32, 599 (1982) as taken from *Int. Poly. Sci. Tech.*, 10, 89 (1983).

S. Kato et al., *J. Organomet. Chem.*, 51, 167–171 (1973).

P. I. Kordomenos et al., *Macromolecules*, 14, 1434–1437 (1981).

M. A. H. Laramay et al., *J. Am. Chem. Soc.*, 112, 9421–9422 (1990).

M. A. H. Laramay et al., *Z. Anorg. Allg. Chem.*, 605, 163–174 (1991).

C. Lensink et al., *J. Am. Chem. Soc.*, 111, 3478–3479 (1989).

E. Martelli et al., *J. Mol. Catal.*, 22, 89–91 (1983).

J. Mizuya et al., *J. Polym. Sci.:* Part A, 29, 1545–1548 (1991).

H. Schmidt et al., *Z. Anorg. Allg. Chem.*, 578, 78–80 (1989).

H. Schmidt et al., *Phosphorus, Sulfur and Silica*, 49/50, 163–168 (1990).

Y. Taguchi et al., *Bull. Chem. Soc. Jpn.*, 63, 3486–3489 (1990).

J. S. Tang et al., "Stepwise Transannular Bond Formation Between Bridgehead Atoms in Z-P(-MeNCH$_2$CH$_2$)$_3$N Systems" abstract of paper presented at Am. Chem. Cos. Meeting, San Francisco, Calif., Apr. 5–10, 1992.

J. S. Tang et al., *J. Am. Chem. Soc.*, 114, 3129–3131 (1992).

H. Ulrich, *J. Cell. Plast.*, 31–34 (Jan./Feb.: 1981).

J. G. Verkade, "Five-Coordinate and Quasi--Five-Coordinate Phosphorus", ACS Symposium Series developed from the 202nd National Meeting of Am. Chem. Soc., New York, N.Y., Aug. 25–30, 1991.

S. K. Xi et al., *Inorg. Chem.*, 29, 2214–2220 (1990).

S. Wong et al., *J. Polym. Sci:* Part A, 24, 2867–2875 (1986).

*Primary Examiner*—John M. Ford
*Attorney, Agent, or Firm*—Merchant, Gould, Smith, Edell, Welter & Schmidt

[57] ABSTRACT

A method is provided to prepare triaryl isocyanurates from aryl isocyanates by using triazaprophosphatrane catalysts.

17 Claims, No Drawings

METHOD FOR SYNTHESIS OF TRIARYLISOCYANURATES FROM ARYL ISOCYANATES USING TRIAZAPROPHOSPHATRANE CATALYSTS

This is a continuation-in-part of our copending application, Ser. No. 07/948,168, filed Sep. 21, 1992.

BACKGROUND OF THE INVENTION

This invention has been made with the support of National Science Foundation Grant No. CHE-8908136. The U.S. Government has certain rights in the invention.

Triaryl isocyanurates of general formula 1:

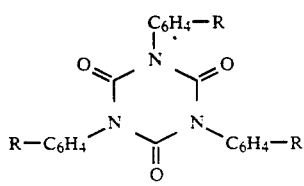

wherein $C_6H_4$ is 1,4-phenylene, 1,2-phenylene or 1,3-phenylene and R is, for example, 2-, 3- or 4-halo, H, methyl or methoxy, are useful as activators for the continuous anionic polymerization and post-polymerization of ε-caprolactam to nylon-6. These activators yield a final product having a low content of unreacted monomer and a highly stable melt viscosity. See, for example, Z. Bukac et al., *Czech. CS* 227,247 (*Chem. Abstr.*, 105, 173224r (1986)); Z. Bukac et al., *Chem Prum.*, 35, 361 (1985) (*Chem. Abstr.*, 103, 123978c (1984)); J. Horsky et al., *Int. Polym. Sci. Tech.*, 9, 65 (1982). Recently, the superior thermal and hydrolysis stability of triphenyl isocyanurate-based foams and plastics have generated considerable interest in the development of methods to produce trimers of general formula 1. See, H. Ulrich, *J. Cellular Plastics*, 17, 31 (Jan./Feb. 1981), P.I. Kordomenas et al., *Macromolecules*, 14, 1434 (1981) and D.K. Hoffman, *J. Cellular Plastics*, 20, 129 (1984).

Since impurities in the activators of formula 1 lower the quality of nylon-6, attempts have been made to develop purification methods for these trimers. However, due to the complexity of the processes which have been used, only relatively low yields of pure products have been obtained. See, Z. Bukac et al., cited above.

Several catalytic methods to prepare triaryl isocyanurates have been reported. For example, Y. Taguchi et al., *Bull. Chem. Soc. Japan*, 63, 3486 (1990) reported the trimerization of phenyl isocyanate in the presence of amine catalysts in 22-100% yield using high pressures. S. Kato et al., *J. Organometallic Chem.*, 51, 167 (1923) trimerized phenyl isocyanate to yield 1 (R=H) in 82% yield, using [α-(trimethylstannyl)phenacyl]triphenylphosphonium ylide. E. Martilli et al., *J. Molec. Catal.*, 22, 89 (1983) reported the use of $(\eta^5\text{-}C_5H_4Me)Mn(CO)_3$ and photolysis to catalyze the same reaction in 80% yield. J. Mizuya et al., *J. Polymer Sci.: Part A: Polymer Chem.*, 29, 1545 (1991) accomplished the same reaction in relatively low yields (72-80%) using large amounts of alkoxyalkenes as catalysts. However, the more electrophillic isocyanate, 4-methylphenyl isocyanate, did not cyclotrimerize under these conditions. K. Ashide, EPA 169,708 (*Chem. Abstr.*, 107, 134825j (1987)) trimerized phenylisocyanate to 1 (R=H) in only 63% by using 10% silicates as the catalyst.

Therefore, a continuous need exists for methods to prepare triarylisocyanurates in high yields, which require little or no purification of the final product. A further need exists for methods to prepare triisocyanurates under mild reaction conditions using non-toxic, non-metallic catalysts.

SUMMARY OF THE INVENTION

The present invention provides a method for preparing triarylisocyanurates comprising reacting an aryl isocyanate of the general formula 3:

$$RArN=C=O \quad (3)$$

wherein Ar is 1,3-phenylene, 1,2-phenylene or 1,4-phenylene and R is H, halo (F, Cl, Br or I), $(C_1\text{-}C_5)$alkyl or $(C_1\text{-}C_5)$alkoxy with or without a solvent in the presence of catalytic amount of a compound of the general formula 2:

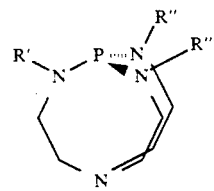

wherein R', R" and R''' are each H, $(C_1\text{-}C_8)$alkyl, $(C_6\text{-}C_9)$aryl, or $(alk)_3Si$, wherein each alk is $(C_1\text{-}C_4)$alkyl, preferably to yield a compound of the formula 1:

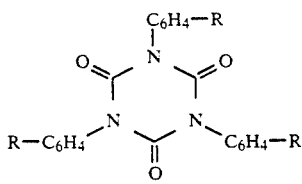

wherein R is as defined above.

R can be in the 2, 3 or 4 position of the Ar ($C_6H_4$) ring. Preferably, R', R" and R''' are the same substituents. The term "aryl" includes alkylaryl or aralkyl and is preferably benzyl. The term "$(C_1\text{-}C_8)$alkyl" includes branched or straight-chain alkyl, as well as $(C_3\text{-}C_8)$cycloalkyl or $(C_3\text{-}C_8)$cyclyalkylalkyl, and is preferably $(C_1\text{-}C_4)$alkyl, e.g., methyl or ethyl. The catalyst can catalyze the reaction with or without solvent in the reaction mixture. Preferably, a solvent is used. A wide range of organic solvents can be employed and include ethers (tetrahydrofuran, diethyl ether), alkanes (hexane, pentane), aromatic solvents (toluene, benzene), dimethyl formamide (DMF), dimethylsulfoxide (DMSO), or acetonitrile. Preferably, the solvent is selected so that the reactants are soluble therein at the temperature at which the trimerization is carried out, but the product 1 is insoluble in the solvent, preferably below 25° C. Thus, only simple filtration is needed to obtain highly pure, solid triaryl isocyanurates.

The temperature can also be varied widely, e.g., from room temperature (20°-25° C.) to the refluxing temperature of the selected organic solvent (i.e., 150°-200° C). Preferably, the trimerization reaction is carried out at about 60°-70° C., in an aromatic solvent.

For example, in accord with the present method triaryl isocyanurates of formula 1 have been prepared from aryl isocyanates in 95–96% yield with 100% purity by using 0.33% trimethyl-triazaprophosphatrane 2a as the catalyst and by using benzene as the solvent. No purification except filtration of the reaction products is necessary to obtain highly pure compounds of formula 1.

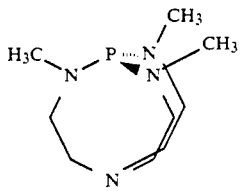

(2)

Thus, the catalyst 2 used in the present invention catalyzes trimerization of aryl isocyanates effectively under mild conditions to yield the desired triaryl isocyanurates 1 in high yield and without any by-products. Electron-donating groups on the phenyl group in aryl isocyanates make them very difficult to trimerize. Thus, as found by Mizuya et al., cited above, compounds such as alkoxyallenes with weak catalytic properties cannot catalyze trimerization of even the weakly electron-donating p-methyl-substituted phenyl isocyanate to its corresponding isocyanate. Compound 2 used in this invention is, however, strongly catalytic. Thus, it almost quantitively catalyzes the trimerization not only of phenyl isocyanate, but also of the strongly electron-donating p-methoxy substituted phenyl isocyanate to the corresponding trimers 1 (R=H, p-MeO, respectively).

The method in the present invention also is advantageous in that the reaction may be carried out without a solvent, and that it uses a very small amount (i.e., about 0.25–5 mol-%) of the catalyst as a mol-% of the isocyanate and produces triisocyanurates in high yields (90%) in relatively short reaction times.

DETAILED DESCRIPTION OF THE INVENTION

As illustrated in the examples and in J.G. Verkade (U.S. Pat. No. 5,051,533), the compounds of formula 2 can be made by a straightforward pair of reactions. In the first step a trisubstituted tris-N-alkyl-2-aminoethylamine (trialkyl-TREN) is reacted, preferably with an equimolar amount of bis-dimethylaminochlorophosphine, to provide the phosphatranyl chloride in Scheme 1.

Scheme 1

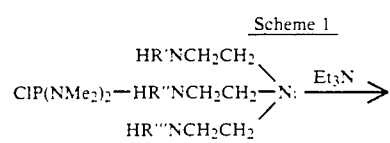

-continued
Scheme 1
trialkyl-TREN

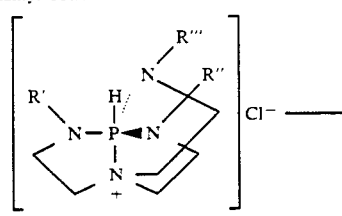

phosphatranyl chloride

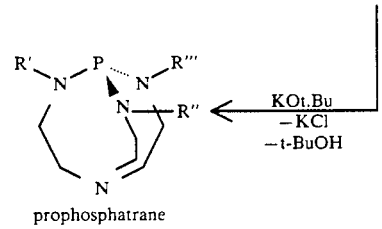

prophosphatrane

It is possible to accomplish the reaction in the absence of a solvent, or in the presence of an organic solvent, with no criticality of temperature. Suitable solvents include chlorinated hydrocarbons, aromatic hydrocarbons, and ethers. A highly preferred solvent is methylene chloride. This reaction proceeds in an essentially stoichiometric fashion. The starting compound, (TREN), wherein R'=R''=R'''=H, is commercially available from Aldrich Chem. Co. or W.R. Grace and Company, and can be converted to trimethyl-TREN as described in Example 1. In the second step of the synthesis, the phosphatranyl chloride is converted to the prophosphatrane in the presence of an organic base such as potassium tertiary butoxide in acetonitrile solvent at room temperature.

The invention will be further described by reference to the following detailed examples.

EXAMPLE 1

Synthesis of Trimethyl-TREN((HCH$_3$NCH$_2$CH$_2$)$_3$N) (4)

In accord with the procedure of H. Schmidt et al., Z. anoro. allq. Chem., 578, 75 (1989), ethylchloroformate (33.4 g, 0.310 mol) was added dropwise to a solution of tris(2-aminoethyl)amine (TREN) (29.2 g, 0.20 mol) dissolved in a mixture of benzene (225 mL) and water (100 mL) cooled to 5° C. After the addition was completed, KOH (36.4 g, 0.650 mol) dissolved in water (35 mL) was added dropwise simultaneously with more ethylchloroformate (33.4 g, 0.310 mol). The reaction mixture was stirred for 2 hr. at 5° C. and then for 8 hr. at room temperature. The benzene layer was separated and the water layer extracted with chloroform (2×100 mL). The combined organic fractions were dried over MgSO$_4$, decanted and the decantate evaporated to dryness to give the intermediate tris(2-carbethoxyaminoethyl)amine (5) in 85% yield as a thick oil which was used in subsequent reactions without further purification ($^1$H NMR (CDCl$_3$)δ1.27 (9H, t, $^3J_{HH}$=7.1 Hz), δ2.60 (6H, t, $^3J_{HH}$=5.7 Hz), δ3.23 (6H, br), δ4.10 (6H, q, $^3J$=7.1 5.50 (3H, br); IR 3300, 1720, 1530, 1250 cm$^{-1}$).

A solution of 5 (61.3 g, 0.170 mmol) in THF (250 mL) was added dropwise to a suspension of LiAlH$_4$ (30.0 g, 0.79 mol) in THF (700 mL). The reaction mixture was heated at reflux temperature overnight. Water (50 mL) and a solution of KOH (50 g) in water (50 mL) were carefully added. The solution was decanted from the inorganic gel. Removal of the solvent from the decantate yielded a yellow oil which upon distillation yielded product 4 in 88% yield as a colorless liquid (m/e 189.2082 (calcd, 189.20793 for M+H)); $^{31}C$ NMR (CDCl$_3$)$\delta$54 1 (CH$_2$), $\delta$49.6 (CH$_2$), $\delta$36.3 (CH$_3$); $^1$H NMR (CDCl$_3$)$\delta$1.30 (3H, br, NH), $\delta$2.39 (9H, s, CH$_3$), $\delta$2.48 (6H, m, $^3J_{HH}$=6.1 Hz)$\delta$2.52 (6H, m $^3J_{2HH}$=6.1 Hz).

EXAMPLE 2

P(CH$_3$NCH$_2$CH$_2$)$_3$N (2a)

Method A: P(NMe)$_3$ (8.8 g, 54 mmol) and 4 (10 g, 53 mmol) were dissolved in dry xylene (60 mL) and heated at reflux for 21 days. The solvent was removed under vacuum. Sublimation of the resulting thick oil at 105° C./0.05 mm Hg afforded 2a in 46% yield (5.3 g, 24.5 mmol) as a colorless waxy solid (m/e 216.15088 (calcd. 216.15039 for M)); IR 332 s, 1303 m, 1244 s, 1226 s, 1197 m, 1145 s, 1128 s 1053 s, 1004 s, 960 w, 887 m, 850 s, 767 w, 650 s, 634 s cm$^{-1}$.

Method B: A solution of 4 (1.67 g, 11.4 mmol) in CH$_2$Cl$_2$ (20 mL), is added over a period of 5 min to a stirred solution of ClP(NMe$_2$)$_2$(1.76 g. 11.4 mmol) and Et$_3$N 1.5 g, 15 mmol) in CH$_2$Cl$_2$(30 mL). Stirring at room temperature for 1 hr., followed by removal of the solvent and Et$_3$N afforded the phosphatranyl chloride in essentially quantitative yield. The salt was recrystallized from hexane/chloroform at $-20°$ C. to give an 82% yield of the product as a colorless crystalline solid. Treatment of the compound (Cl$^-$) with AgBF$_4$ in CH$_2$Cl$_2$ gave the BF$_4$$^-$salt in quanlitative yield. X-ray crystallography of the BF$_4$$^-$ salt confirmed the presence of the phosphatranyl cation phosphatrane wherein R', R" and R''' are methyl.

The chloride was converted to the corresponding prophosphatrane by adding 0.87 g (3.4 mmol) of the salt dissolved in 10 mL of acetonitrile to a suspension of potassium tertiary butoxide (0.41 g, 3.7 mmol) in acetonitrile (20 mL). After stirring the reaction mixture for 30 minutes at room temperature, the solvent was removed under vacuum and the residue extracted with 2×30 mL of hexanes. The white residue was purified by vacuum sublimation (60° C./0.01 mm Hg) to give the prophosphatrane 2a (R'=R"=R'''=Me) in 82% yield.

EXAMPLE 3

To a solution of 2a (0.11 g, 0.50 mmol) in dry benzene (10 mL) was added by syringe phenyl isocyanate (18.03 g, 99% pure, 150 mmol, Aldrich). The mixture was stirred at room temperature. A white precipitate formed rapidly after 3 minutes of stirring. Then the mixture solidified into a solid mass in a few seconds. The solid mass was cooled to room temperature and evaporated under vacuum (with oil pump) to remove the solvent. The residue was ground to powder and then stirred with 30 mL of dry benzene for 2 hr, filtered in vacuo, further washed with 15 mL of dry benzene and finally dried in vacuo to give 17.24 g (96.6%) of TLC-pure triphenyl isocyanurate (1, R=H); m.p. of 279.0°-14 279.5° C. The structure and purity of 1 (R=H) were confirmed by $^1$H NMR, IR and HRMS analyses.

EXAMPLE 4

To 0.11 g (0.50Q mmol) of 2a was added by syringe phenyl isocyanate (18.03 g, 99% pure, 150 mmol, Aldrich). The mixture was stirred at room temperature. A white precipitate formed rapidly after 2 minutes of stirring. A solid mass appeared in a few seconds. The solid mass was ground to powder and then stirred with 30 mL of dry benzene, filtered in vacuo, further washed with 10 mL of dry benzene and finally dried in vacuo to give 16.86 g (94.4%) of TLC-pure triphenyl isocyanurate (1, R=H); m.p. of 279.0°-279.5° C. The structure and purity of 1 (R=H) we firmed by $^1$H NMR, IR and HRMS analyses.

EXAMPLE 5

To a solution of 2a (0.06 g, 0.3 mmol) in dry benzene (5 mL) was added by syringe p-methoxyphenyl isocyanate (11.30 g, 99% pure, 75 mmol, Aldrich). The mixture was stirred at room temperature. After 3 minutes of stirring, a white precipitate formed gradually. The mixture solidified in another 5 minutes. The solid was cooled to room temperature, evaporated under vacuum to remove the solvent. The residue was ground to powder and then stirred with 50 mL of dry benzene, filtered in vacuo, further washed with 30 mL of dry benzene and finally dried in vacuo in 50° C. to give 11.05 g (98.7%) of TLC-pure tri-p-methoxyphenyl isocyanurate (1, R=p-methoxy); m.p. of 261.0°-261.5° C. The structure and purity of 1 (R=H) were confirmed by $^1$H NMR, IR and HRMS analyses.

EXAMPLE 6

To 0.06 g (0.3 mmol) of 2a was added by syringe p-methoxyphenyl isocyanate (11.30 g, 99% pure, 75 mmol, Aldrich). The mixture was stirred at room temperature. After 5 minutes of stirring, a white precipitate formed very rapidly. The mixture solidified in a few seconds. The solid was cooled to room temperature, ground to powder and then stirred with 50 mL of dry benzene. The solids were filtered in vacuo, further washed with 30 mL of dry benzene and finally dried in vacuo in 50° C. to give 10.5 g (93.8%) of TLC-pure tri-p-methoxyphenyl isocyanurate (1, R=p-methoxy); m.p. of 261.0°-261.5° C. The structure and purity of 1 (R=p-methoxy) were confirmed by $^1$H NMR, IR and HRMS analyses.

EXAMPLE 7

[HP(NHCH$_2$CH$_2$)$_3$N]Cl, 2b.HCl(2.HCl, R'=R"=R'''=H).

A solution containing 1.215 g (8.853 mmol) of PCl$_3$ in 5.0 mL of CH$_2$Cl$_2$ was added at once to a solution containing 2.889 g (17.70 mmol) of P(NMe$_2$)$_3$ in 25 mL of CH$_2$Cl$_2$. This solution was then cooled to 5° C. and 3.882 g (26.55 mmol) of tris(2-aminoethyl)amine in 25 mL of CH$_2$Cl$_2$ was added over a period of 15 minutes. The resulting precipitate was separated by filtration and washed with 25 mL of CH$_2$Cl$_2$ (5.581 g, quantitative yield). The precipitate was spectroscopically pure according to the $^1$H, $^{13}$C and $^{31}$P NMR spectra.

EXAMPLE 8

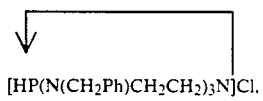

[HP(N(CH$_2$Ph)CH$_2$CH$_2$)$_3$N]Cl,

2c·HCl(2·HCl, R'=R''=R'''=CH$_2$Ph)

A solution containing 0.233 g (1.70 mmol) of PCl$_3$ in 5 mL of CH$_2$Cl$_2$ was added all at once to a solution containing 0 555 g (3.41 mmol) of P(NMe$_2$)$_3$ in 10 mL of CH$_2$Cl$_2$. To this solution was slowly added a solution containing 2.12 g (5.11 mmol) of tris-(N-benzyl-2-aminoethyl)amine in 10 mL of CH$_2$Cl$_2$. The reaction mixture was stirred at room temperature for one hour. The volatiles were then removed and the white solid residue was washed with hexanes giving 2.40 g (98% yield) of spectroscopically pure 2c·HCl.

EXAMPLE 9

P[N(CH$_2$Ph)CH$_2$CH$_2$]$_3$N, 2d (2, R'=R''=R'''=CH$_2$Ph)

To a solution containing 0.572 g (5.11 mmol) of KO-t-Bu in 20 mL of THF was added a solution containing 2.21 g (4.64 mmol) of 2c·HCl in 20 mL of THF. After stirring the reaction mixture at room temperature for one hour, the volatiles were removed in vacuo. The residue was extracted with several 100 mL portions of hexanes for 3 hours. The extracts were collected and the hexanes removed in vacuo to give an oily residue which was spectroscopically pure 2d. ($^{31}$P NMR (Et$_2$O)δ128.3 (s); $^1$H NMR (C$_6$D$_6$)δ 7.30 (15 H, m, C$_6$H$_5$, δ4.04 (6 H, d, $^3J_{P-H}$=12.1 Hz, δ2.71 (12H, br, NCH$_2$); $^{13}$C NMR (C$_6$D$_6$)δ40.6 (d, PhCH$_2$, $^3J_{P-H}$=15.2 Hz), δ50.2 (s, N$_{eq}$CH$_2$), δ54.7 (s, N$_{ax}$CH$_2$), δ128.0 (s, C$_6$H$_5$), δ128.3 (s, C$_6$H$_5$), δ129.4 (s, C$_6$H$_5$), δ138.1 (s, C$_6$H$_5$); HRMS: m/e (measured) 444.24374, m/e (calculated) 444.24429 for C$_{27}$H$_{33}$N$_4$P).

EXAMPLE 10

[H(SiMe$_3$)NCH$_2$CH$_2$]$_3$N (6)

In accord with the procedure of D. Gudat et al., Orqanometallics, 8, 2772 (1989), a solution of 2.00 g (13.7 mmol) of TREN in 35 ml of THF was cooled to −50° C., and 20.5 ml of a 2 M solution of η-butyl lithium in hexanes was slowly added. The mixture was allowed to warm to room temperature and was stirred for an additional hour. The mixture was evaporated to dryness and the residue was suspended in 50 ml of ether and was stirred for 30 minutes. After filtration and evaporation of the solvent, the residue was distilled, affording 2.66 g of 6 as a colorless liquid (bp 80°-90° C., yield 54%).

EXAMPLE 11

HP[N(SiMe$_3$)CH$_2$CH$_2$]$_3$N, 2e·HCl(2·HCl, R'=R''=R'''=SiMe$_3$

A solution containing 1.22 g (8.85 mmol) of PCl$_3$ in 5.0 ml of CH$_2$Cl$_2$ is added at once to a solution containing 2.89 g (17.70 mmol) of P(NMe$_2$)$_3$ in 25 ml of CH$_2$Cl$_2$. This solution is then cooled to 5° C. and 9.62 g (26.55 mmol) of 6 is added over a period of 15 minutes. The resulting precipitate is separated by filtration and washed with 25 ml of CH$_2$Cl$_2$ to yield the title compound.

EXAMPLE 12 p[(SiMe$_3$)NCH$_2$CH$_2$]$_3$N (2e)(2, R'=R''=R'''=SiMe$_3$)

To a solution containing 0.57 g (5.11 mmol) of KO-t-Bu in 20 ml of THF is added a solution containing 2.18 g (4.64 mmol) of 2e·HCl in 20 ml of THF. After stirring the reaction mixture at room temperature for one hour, the volatiles are removed in vacuo. The residue is extracted with several 100 ml portions of hexanes for 3 hours. The extracts are collected and the hexanes are removed in vacuo to give the title compound.

EXAMPLE 13

To a solution of trimethyl-triazaprophosphatrane 2 a (0.11 g, 0.50 mmol) in dry benzene (80 mL) was added by syringe, phenyl isocyanate (18.03 g, 99% pure, 150 mmol, Aldrich). The mixture was stirred and heated at 60°-70° C. for 40 hr., then allowed to stand at room temperature for 10 hr. The white precipitate was filtered in vacuo (oil pump) and dried in vacuo to give 16.8 g (94%) of TLC pure triphenyl isocyanurate (1, R=H); m.p. 279.0°-279.5° C. The structure and purity of compound 1, R=H, was further confirmed by $^1$H NMR, $^{13}$C NMR, IR, HRMS and elemental analyses. The mother liquor was concentrated to about 50 mL, filtered and washed with dry benzene (5 mL×2) to give 0.41 g of triphenyl isocyanurate (1, R=H) which was also TLC pure. The total yield was 96%.

EXAMPLE 14

To a solution of 2 a (0.11 g, 0.50 mmol) in dry benzene (80 mL) was added by syringe p-methoxyphenyl isocyanate (22.60 g, 99% pure, 150 mmol, Aldrich). The mixture was stirred and heated at 60°-70° C. for 72 hr. and allowed to stand at room temperature for 10 hr. The precipitate was filtered in vacuo (oil pump), washed with dry benzene (15 mL×2) and dried in vacuo to give 21.47 g (95%) of TLC-pure tri(p-methoxy phenyl)isocyanurate (1, R=p-MeO); m.p. of 261.0°-261.5° C. The structure and purity of 1 (R=p-MeO) were further confirmed by $^1$H NMR, IR and HRMS analyses.

Compounds of the formula 2 are believed to be the most potent catalysts known for trimerizing isocyanates. They can be used effectively in very small amounts. They are also fast catalysts under mild conditions, since the trimerization reaction starts spontaneously at room temperature (20°-30° C.) and is completed in a few minutes, giving a virtually quantitative yield of essentially pure product.

All publications and patents are herein incorporated by reference to the same extent as if each individual publication or patent application was specifically and individually indicated to be incorporated by reference.

It will be apparent to one of ordinary skill in the art that many changes and modifications can be made in the invention without departing from the spirit or scope of the appended claims.

What is claimed is:

1. An improved process for preparing triarylisocyanurates by reacting an aryl isocyanate of the general formula (3):

$$RC_6H_4N=C=O \qquad (3)$$

wherein C$_6$H$_4$ is 1,3-phenylene, 1,2-phenylene or 1,4-phenylene and R is H, halo (C$_1$-C$_5$)alkyl or (C$_1$-C$_5$)alkoxy; to yield a compound of the formula (1):

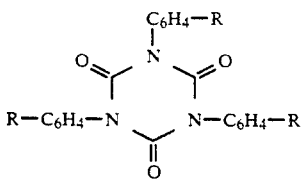

(1)

wherein R is as defined above; wherein the improvement comprises carrying out the reaction in the presence of a catalytic amount of a compound of the general formula (2):

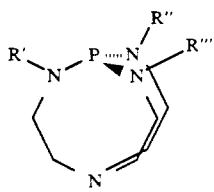

(2)

wherein R', R" and R'" are each H, $(C_1-C_8)$alkyl, $(C_6-C_9)$aryl or $(alk)_3Si$, wherein each alk is $(C_1-C_4)$alkyl.

2. The process of claim 1 wherein the improvement further comprises carrying out the reaction without solvent.

3. The process of claim 1 wherein $C_6H_4$ is 1,4phenylene.

4. The process of claims 1 or 3 wherein R is halo.

5. The process of claim 4 wherein R is 4'-chloro.

6. The process of claims 1 or 3 wherein R is $(C_1-C_5)$alkyl.

7. The process of claim 6 wherein R is 4'—$CH_3$.

8. The process of claim 1 wherein R is H.

9. The process of claim 1 or 8 wherein R', R" and R'" are each $(C_1-C_4)$alkyl.

10. The process of claim 9 wherein R', R" and R'" are $CH_3$.

11. The process of claims 1 or 8 wherein R', R" and R'" are benzyl.

12. The process of claims 1 or 8 wherein R', R" and R'" are trimethylsilyl.

13. The process of claim 1 wherein the reaction is carried out in an organic solvent.

14. The process of claim 13 wherein the reaction is carried out at about 60°-70° C. in an aromatic solvent.

15. The process of claim 14 wherein the solvent is benzene.

16. The process of claims 13 wherein the compound of formula 1 is separated by filtration from the organic solvent, the compound of formula 2 and the compound of formula 3.

17. The process of claim 1 wherein about 0.25-5 mol-% of the compound of formula 2 is used.

* * * * *

UNITED STATES PATENT AND TRADEMARK OFFICE
CERTIFICATE OF CORRECTION

PATENT NO. : 5,260,436

DATED : November 9, 1993

INVENTOR(S) : Verkade et al.

It is certified that error appears in the above-identified patent and that said Letters Patent is hereby corrected as shown below:

In column 2, line 19, please insert --a-- after the word "of"

In column 2, line 33, please insert --$CH_3$-- after the word "preferably"

In column 2, line 49, please delete "cyclyalkylalkyl" and insert --cycloalkylalkyl--

In column 4, line 13, please delete "(2)" and insert --(2a)--

In column 3, line 46, please delete "(90%)" and insert --($\geq$ 90%)--

In column 4, line 47, please delete "anoro allq" and insert --anorg. allg--

In column 4, line 65, please insert --Hz) , $\delta$-- after the numeral "7.1"

In column 5, line 9, please delete "54  1" and insert --54.1--

In column 5, line 23, please delete "332s" and insert --1332s,--

In column 5, line 37, please delete "quanlitative" and insert --quantitative--

In column 5, line 66, please delete "14" after "279.0°-"

In column 6, line 3, please delete "(0.50Q mmol)" and insert --(0.50 mmol)--

In column 6, line 14, please delete "we firmed" and insert --were confirmed--

In column 7, line 13, please delete "0 555" and insert --0.555--

In column 7, line 36, please delete "3J" and insert "2J"

UNITED STATES PATENT AND TRADEMARK OFFICE
CERTIFICATE OF CORRECTION

PATENT NO. : 5,260,436

DATED : November 9, 1993

INVENTOR(S) : Verkade et al.

It is certified that error appears in the above-identified patent and that said Letters Patent is hereby corrected as shown below:

In column 8, line 2, please delete "p" and insert --P--

Signed and Sealed this

Eighth Day of July, 1997

Attest:

BRUCE LEHMAN

Attesting Officer

Commissioner of Patents and Trademarks